United States Patent
Karube et al.

(10) Patent No.: US 7,306,705 B2
(45) Date of Patent: Dec. 11, 2007

(54) METHOD FOR DEHYDRATING COMPOSITION COMPRISING LITHIUM BIS(PENTAFLUOROETHANESULFONYL)IMIDE

(75) Inventors: Daisuke Karube, Settsu (JP); Shintaro Ogata, Settsu (JP); Keiko Washino, Settsu (JP); Tatsuya Otsuka, Settsu (JP)

(73) Assignee: Daikin Industries, Ltd., Osaka-shi (JP)

( * ) Notice: Subject to any disclaimer, the term of this patent is extended or adjusted under 35 U.S.C. 154(b) by 0 days.

(21) Appl. No.: 10/201,311

(22) Filed: Jul. 24, 2002

(65) Prior Publication Data

US 2003/0022069 A1     Jan. 30, 2003

(30) Foreign Application Priority Data

Jul. 26, 2001   (JP) .............................. 2001-225755

(51) Int. Cl.
  *B01D 3/10*   (2006.01)
  *B01D 3/34*   (2006.01)
  *H01M 10/40*  (2006.01)

(52) U.S. Cl. ........................... 203/14; 203/51; 203/58; 203/60; 203/62; 203/91; 429/325; 429/337; 429/339; 429/341; 429/342; 429/347

(58) Field of Classification Search ................ 203/14, 203/57, 38, 91, 60, 62, 58, 51; 562/301, 562/124; 564/82; 429/337–339, 341, 342, 429/347, 325

See application file for complete search history.

(56) References Cited

U.S. PATENT DOCUMENTS 5,395,486 A * 3/1995 Killian et al. ................. 203/14
6,383,688 B1 * 5/2002 Inagaki et al. .............. 429/322

FOREIGN PATENT DOCUMENTS

| EP | 0550200 B1 |   | 3/1996 |
| JP | 58-028174 |   | 2/1983 |
| JP | 06-023209 |   | 2/1994 |
| JP | 10-338653 |   | 12/1998 |
| WO | 96/30487 | * | 10/1996 |
| WO | 00/38813 | * | 7/2000 |

* cited by examiner

*Primary Examiner*—Virginia Manoharan
(74) *Attorney, Agent, or Firm*—Kratz, Quintos & Hanson, LLP

(57) ABSTRACT

A method for dehydrating an aqueous composition comprising lithium bis(pentafluoroethanesulfonyl)imide and at least one organic solvent, wherein a part of solvent is distilled off by distillation.

4 Claims, No Drawings

METHOD FOR DEHYDRATING COMPOSITION COMPRISING LITHIUM BIS(PENTAFLUOROETHANESULFONYL)IMIDE

TECHNICAL FIELD

The present invention relates to a method for dehydrating a composition comprising lithium bis(pentafluoroethanesulfonyl)imide. A solution of dissolved lithium bis(pentafluoroethanesulfonyl)imide in an organic solvent is a useful substance as an organic ion conductor, and can be used as an electrolytic solution for lithium batteries and the like.

BACKGROUND ART

The electrolytic solution for lithium batteries is extremely incompatible with water. Even a trace amount of water causes the problems such as inactivating the surface of a lithium negative electrode by reacting therewith to form an oxide film, and raising the internal impedance of a battery by forming air bubbles. For this reason, it is important to sufficiently perform a refining dehydration of an electrolytic solution for the improvement of battery quality.

The method for dehydrating a composition comprising lithium bis(pentafluoroethanesulfonyl)imide as an electrolyte is not well known heretofore. JP6-23209A discloses a method where a bis-sulfonimide salt having a $C_1$-$C_4$ perfluoroalkyl group of atoms is mixed with an inert fluorochemical to volatilize water and the inert chemical. In order to apply this method to lithium bis(pentafluoroethanesulfonyl)imide, we attempted the dehydration using perfluorohexane as an inert fluorochemical. However, the water obtained from the salt was at a level of 1000 ppm and the most satisfactory result was not achieved. Moreover, this method is not economically excellent due to the use of an expensive inert fluorochemical.

Disclosed in JP10-338653A is a method for dehydrating a solution of lithium bis(trifluoromethylsulfonyl)imide, which is an analogous compound of lithium bis(pentafluoroethanesulfonyl)imide, wherein a dry inert gas is brought into contact therewith to evaporate water. The method needs circulation of the generated aqueous inert gas for dry through a dehydration system. In order to dehydrate the gas sufficiently by cooling it is necessary to operate a compressor and a refrigerator over a long time, which is not exactly economical.

As a method for producing a nonaqueous electrolytic solution for batteries, JP58-28174A discloses a method where a solvent and a solute are dissolved before water is removed as a part of the solvent being removed by distillation under a reduced pressure.

The publication indicates as an example the dehydration method by dissolving lithium perchlorate in propylene carbonate and removing propylene carbonate by distillation. However, the water contents per perchlorate when evaporating 10% and 20% amount of solvent are both remained at 100 ppm, which shows the limit of this method. Moreover, what should be done for the more effective dehydration is not suggested concretely.

The object of the present invention is to completely dehydrate a composition by a simple method, wherein said composition comprises lithium bis(pentafluoroethanesulfonyl)imide whose water content is difficult to be reduced due to its high deliquescence.

DISCLOSURE OF THE INVENTION

The present inventor found out that the water content of lithium bis(pentafluoroethanesulfonyl)imide can be reduced by distillation of a solvent from the lithium bis(pentafluoroethanesulfonyl)imide solution containing water, and accomplished the present invention.

Specifically, the present invention provides a method for dehydrating the aqueous composition comprising lithium bis(pentafluoroethanesulfonyl)imide and at least one organic solvent characterized in that a part of solvent is distilled off by distillation.

Moreover, the present invention provides a method for producing the electolyte composition which comprises lithium bis(pentafluoroethanesulfonyl)imide and at least one organic solvent, which is characterized in that a part of the solvent is distilled to distill off the water together with the solvent.

In addition, the water content of the nonaqueous electrolytic solution to the whole electrolytic solution is preferably 10 ppm or less.

As a solvent, propylene carbonate, ethylene carbonate, butylene carbonate, γ-butyrolactone, γ-valerolactone, sulfolane, 3-methyl sulfolane, dimethylsulfoxide, N,N-dimethylformamide, N-methyloxazolidinone, N-methylpyrrolidone, 1,3-dimethyl-2-imidazolone, diethyl carbonate, ethyl methyl carbonate, 1,2-dimethoxyethane and the like generally used as a solvent for nonaqueous electrolytic solution can be used.

A water content to the lithium bis(pentafluoroethanesulfonyl)imide in the composition before dehydration of a solvent is 100 ppm or more, preferably about 1000 to 10000 ppm. A water content to the lithium bis(pentafluoroethanesulfonyl)imide after distillation is 90 ppm or less, preferably 60 ppm or less, more preferably 40 ppm or less, and most preferably 30 ppm or less. A water content to the whole composition after distillation is 15 ppm or less, preferably 10 ppm or less, more preferably 7 ppm or less, and most preferably 3 ppm or less. For a nonaqueous electrolytic solution, when the concentration of lithium bis(pentafluoroethanesulfonyl)imide is around one mol/l, the water content in the solution can be set to 10 ppm or less, preferably 7 ppm or less by evaporating an organic solvent.

The concentration of lithium bis(pentafluoroethanesulfonyl)imide in the composition before dehydration is not particularly limited. However, since the usual concentration of lithium ion in a nonaqueous electrolytic solution is about one mol, when the composition after dehydration is used as a nonaqueous electrolytic solution, said concentration is one mol/l or less, more preferably 0.8 mol % or less, further preferably 0.7 mol % or less, and most preferably 0.5 mol % or less. The adequate amount of the solvent removed for dehydration is 10-25% in a volume ratio to the amount of the solution before distillation, and further removal and evaporation can be carried out in order to provide the adequate concentration as an electrolytic solution. Although the pressure during distillation is not particularly limited, distillation under reduced pressure is desirable for the reduction of heating energy. Specifically, distillation may be conducted at 100 mmHg or less and preferably at 10 mmHg or less.

Water is contained in the forerun extracted by distillation. The solvent may be recovered and recycled by performing general purification treatment such as distillation after drying by a molecular sieve.

The necessary time for dehydration depends on the throughput, and generally about 0.5 to 10 hours is sufficient.

BEST MODE FOR CARRYING OUT THE INVENTION

The present invention is illustrated more concretely with reference to the following example.

EXAMPLE 1

Lithium bis(pentafluoroethanesulfonyl)imide was dissolved in propylene carbonate and adjusted to the concentration of 0.3 mol/L. The solution contained 1170 ppm of water, and in regarding said water entirely as a water content to the salt of the lithium bis(pentafluoroethanesulfonyl)imide, the water content was 13250 ppm.

The solution was charged into a 100 mL flask and distilled under the condition of reduced pressure at 10 mmHg to extract propylene carbonate at 98° C. After sampling the lithium bis(pentafluoroethanesulfonyl)imide solution remained in the flask to measure its water content by the Karl Fischer technique, the procedure of concentrating the solution by distillation and measuring water content was repeated. Concentrations of the solution, water contents of the solution, and water contents to the salt of lithium bis(pentafluoroethanesulfonyl)imide are shown in Table 1.

TABLE 1

| | | | | |
|---|---|---|---|---|
| Concentration of Solution (mol/l) | 0.34 | 0.40 | 0.63 | 1.08 |
| Water Content of Solution (ppm) | 42.4 | 3.3 | 4.7 | 7.0 |
| Water Content to Salt (ppm) | 430 | 29 | 28 | 27 |

Comparative Example 1

Dehydration of lithium bis(pentafluoroethanesulfonyl)imide containing 7400 ppm of water was conducted in a vacuum dryer under the condition of 0.5 mmHg, 150° C. and 48 hours. As a result, the water content of the obtained salt was 110 ppm. The lithium bis(pentafluoroethanesulfonyl)imide is a highly deliquescent compound and was not easily dried by the usual method.

As to the dehydration of an organic solvent solution of lithium salt, it is heretofore known that even in the case of a compound without deliquescence such as lithium perchlorate, the water content to lithium perchlorate is not more than the extent of 100 ppm (refer to JP58-28174A).

Lithium bis(pentafluoroethanesulfonyl)imide has the molecular weight 3.7 times higher than the one of lithium perchlorate. For the preparation of these solutions with the same lithium salt concentrations, given that the water contents to the lithium salts are the same, the water content of the lithium bis(pentafluoroethanesulfonyl)imide solution would be 3.7 times higher. For this reason, originally it is difficult to obtain the solution with a low water content. Furthermore, since lithium bis(pentafluoroethanesulfonyl)imide is a highly deliquescent compound, it is still more difficult to reduce the water content of the solution thereof.

As to such lithium bis(pentafluoroethanesulfonyl)imide-containing solution, of which a water content in an organic solvent is difficult to reduce, it is clarified by the present invention that the removal or evaporation of the solvent can realizes a far lower water content than 100 ppm, which is heretofore recognized as a water content to the lithium salt, and that the composition with a water content of 10 ppm or less and especially of about 7 ppm can be obtained, which may be used as a nonaqueous electrolytic solution for lithium ion primary batteries or secondary batteries.

The invention claimed is:

1. A method for dehydrating an aqueous composition consisting of water, lithium bis(pentafluoroethanesulfonyl)imide and at least one organic solvent selected from the group consisting of propylene carbonate, ethylene carbonate, butylene carbonate, γ-butyrolactone, γ-valerolactone, sulfolane, 3-methyl sulfolane, dimethylsulfoxide, N,N-dimethylformamide, N-methyloxazolidinone, N-methylpyrrolidone, 1,3-dimethyl-2-imidazolone, diethyl carbonate, ethyl methyl carbonate, and 1,2-dimethoxyethane, wherein a water content to the lithium bis(pentafluoroethanesulfonyl)imide in the composition before dehydration of the solvent is 100 ppm to 13250 ppm and a part of the at least one organic solvent is distilled off together with water.

2. The method according to claim 1, wherein the water content to the lithium bis(pentafluoroethanesulfonyl)imide after distillation is at most 60 ppm.

3. The method according to either claim 1 or claim 2, wherein the concentration of lithium bis(pentafluoroethanesulfonyl)imide in aqueous composition before distillation is 0.7 mol/L or less.

4. The method according to claim 1, wherein the part of the at least one organic solvent is distilled off under reduced pressure.

* * * * *